United States Patent
Apfelbaum et al.

(10) Patent No.: US 6,645,208 B2
(45) Date of Patent: Nov. 11, 2003

(54) OSTEOSYNTHESIS PLATING APPARATUS AND METHOD WITH EXTENSION PLATE

(75) Inventors: Ronald I. Apfelbaum, Salt Lake City, UT (US); Stephan Eckhof, Tuttlingen (DE); Alexander Haas, Dunningen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 10/234,647

(22) Filed: Sep. 3, 2002

(65) Prior Publication Data

US 2003/0074001 A1 Apr. 17, 2003

Related U.S. Application Data

(63) Continuation-in-part of application No. 09/708,806, filed on Nov. 8, 2000.

(51) Int. Cl.$^7$ .............................................. A61B 17/58
(52) U.S. Cl. ............................................ 606/61; 606/60
(58) Field of Search .............................. 606/60, 61, 62

(56) References Cited

U.S. PATENT DOCUMENTS

| | | | |
|---|---|---|---|
| 2,486,303 A | | 10/1949 | Longfellow |
| 4,503,848 A | | 3/1985 | Caspar |
| 5,261,910 A | * | 11/1993 | Warden et al. ................ 606/61 |
| 5,616,142 A | | 4/1997 | Yuan |
| 5,676,666 A | * | 10/1997 | Oxland et al. ................ 606/61 |
| 5,951,557 A | * | 9/1999 | Luter ........................... 606/69 |
| 6,383,186 B1 | * | 5/2002 | Michelson .................... 606/69 |

FOREIGN PATENT DOCUMENTS

| | | |
|---|---|---|
| DE | 86 24 671 | 10/1986 |
| DE | 43 40 398 | 6/1995 |
| EP | 0 773 004 | 5/1997 |

* cited by examiner

Primary Examiner—Roy D. Gibson
Assistant Examiner—Aaron Roane
(74) Attorney, Agent, or Firm—Barry R. Lipsitz; Douglas M. McAllister

(57) ABSTRACT

The invention relates to a method and apparatus for immobilizing adjacent bone segments. An osteosynthesis plating system is provided for fixing or immobilizing several pieces or segments of bone utilizing screws which may be screwed into the segments of bone through openings provided in the osteosynthesis plate. The osteosynthesis plate is pressed against the bone surface by the screws and fixed thereto. In particular, the invention relates to an osteosynthesis extension plate for immobilizing adjacent segments of bone in a second surgery wherein the removal of a previously implanted osteosynthesis plate is avoided. In this manner the disadvantages associated with removal of the previously implanted plate are avoided.

14 Claims, 16 Drawing Sheets

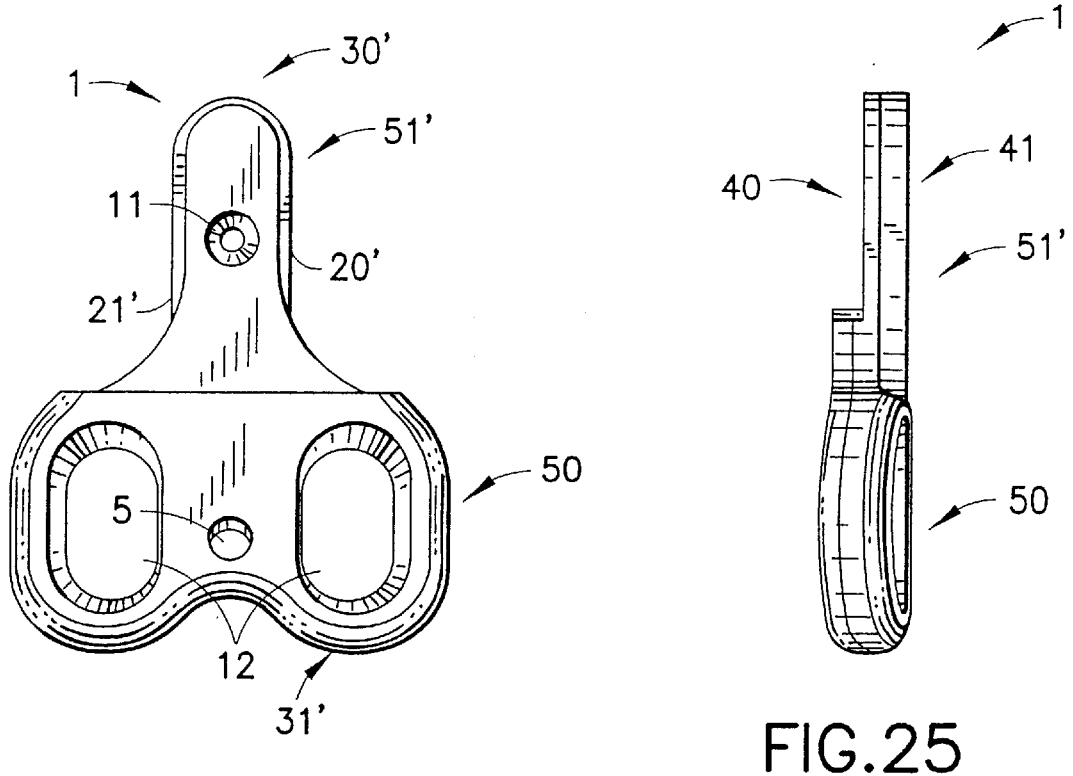
FIG.24
FIG.25
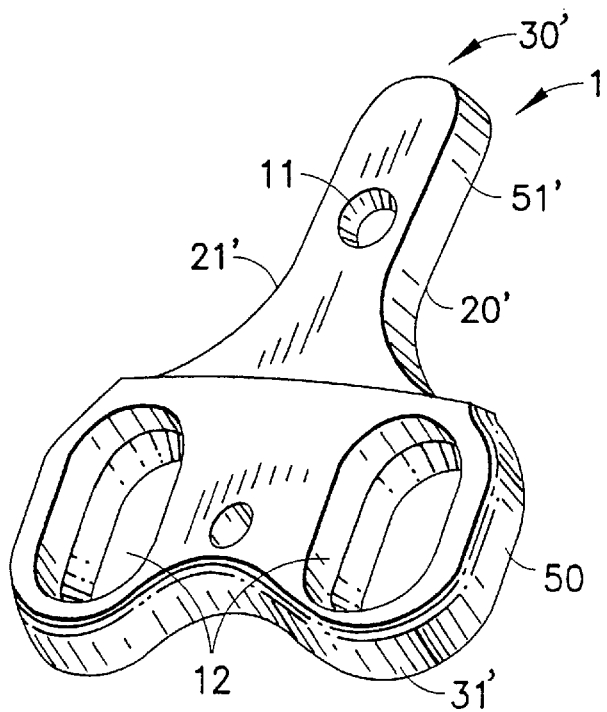
FIG.26

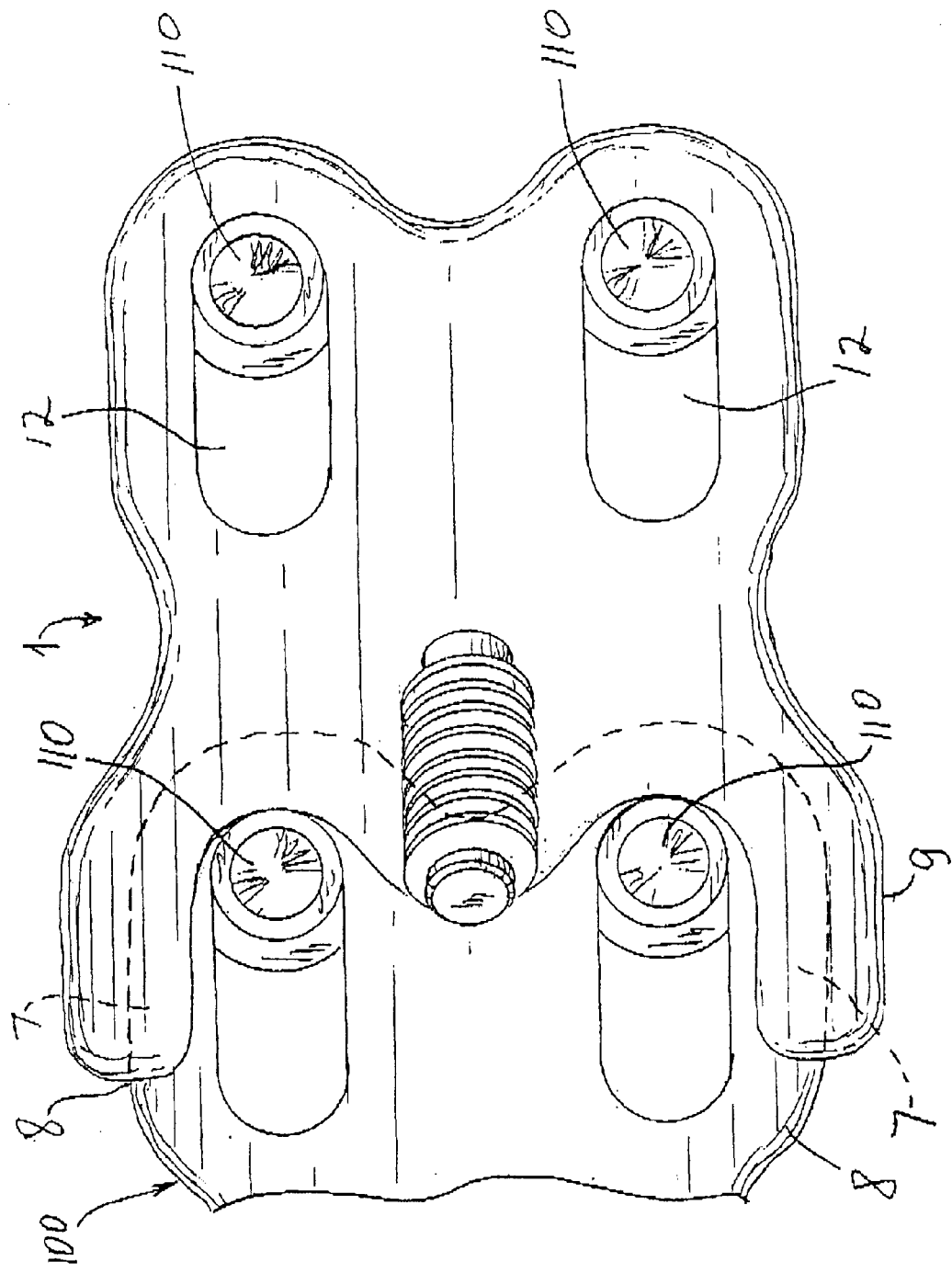

OSTEOSYNTHESIS PLATING APPARATUS AND METHOD WITH EXTENSION PLATE

The present application is a continuation-in-part of U.S. patent application Ser. No. 09/708,806 filed on Nov. 8, 2000.

BACKGROUND OF THE INVENTION

The invention relates to an osteosynthesis plating system for fixing or immobilizing several pieces or segments of adjacent bone utilizing screws which may be screwed into the segments of bone through openings provided in the osteosynthesis plate. The Osteosynthesis plate is pressed against the bone surface by the screws and fixed thereto. In particular, the invention relates to an extension plate for use with a previously implanted osteosynthesis plate for fixing additional adjacent segments of bone during a subsequent surgery.

Skeletal parts in human and animal bodies, particularly articulated skeletal segments, are often immobilized relative to one another to allow for healing of bone injuries, for example after a fracture. Absolute immobilization is paramount for the healing of bone injuries.

For such immobilization purposes, osteosynthesis plates of the type disclosed in U.S. Pat. No. 4,503,848 are utilized in surgical repair and immobilization of bone injuries.

However, typically the need may arise where a second surgery is required to repair bone injuries to adjacent bone segments. The current procedure requires that the previously implanted plate be removed completely in order to replace it with a longer plate such that the adjacent bone segment and the originally immobilized bone segments can now be immobilized by a single osteosynthesis plate. To remove the previously implanted plate, each screw must be removed, some of which screws may be overgrown with bone. Explanting of these screws is a time consuming process which is very invasive and risky for the patient.

The object of the present invention is to provide a system of immobilizing adjacent segments of bone in a second surgery wherein the removal of a previously implanted osteosynthesis plate is avoided. In this manner the disadvantages associated with removal of the previously implanted plate are avoided. Therefore, the advantages provided by the present invention include a reduction in surgery time and a less invasive surgical procedure. In addition, the cost associated with the extension plate is lower compared to a longer replacement plate. Surgical costs are decreased as well due to the reduction in surgical time required.

Corresponding apparatus and methods are provided.

SUMMARY OF THE INVENTION

The invention relates to a method and apparatus for immobilizing adjacent bone segments. An osteosynthesis plating system is provided for fixing or immobilizing several pieces or segments of bone utilizing screws which may be screwed into the segments of bone through openings provided in the osteosynthesis plate (sometimes referred to herein as "bone plate"). The osteosynthesis plate is pressed against the bone surface by the screws and fixed thereto. In particular, the invention relates to an osteosynthesis extension plate for immobilizing adjacent segments of bone in a second surgery wherein the removal of a previously implanted osteosynthesis plate is avoided.

In a particular embodiment, an osteosynthesis extension plate is provided for immobilizing at least two adjacent bone segments by means of screws which may be screwed into the bone segments through openings in the extension plate. The extension plate is generally defined by longitudinal edges and transverse edges, the plate having a greater longitudinal dimension than transverse dimension. The extension plate has a first bone contacting surface and a second non-bone contacting surface. The extension plate is further defined by a thick plate portion and a thin plate portion. At least two rows of pairs of through openings are provided in the extension plate. A first pair of through openings is arranged in the thick portion of the plate and a second pair of through openings is arranged in the thin portion of the plate such that the thin portion of the plate can be inserted underneath and affixed between a second osteosynthesis plate and a bone segment. The thick portion of the extension plate is affixed to an adjacent bone segment by screws, thereby immobilizing an adjacent bone segment.

In a further embodiment of the invention, the thin portion of the extension plate can be positioned underneath the thick portion of an identical extension plate to provide for immobilization of adjacent bone segments. In this manner several identical extension plates can be piggybacked by placing the thin portion of one extension plate underneath the thick portion of another extension plate to immobilize several adjacent bone segments.

In another embodiment of the invention, the extension plate is curved in the direction transverse to its longitudinal axis such that the first bone contacting surface is concave. Such a configuration of the first bone contacting surface allows for better contact with the surface of the bone segment to be immobilized.

In a further embodiment of the invention, the osteosynthesis extension plate is used to immobilize bone segments during a second surgery where a previously implanted osteosynthesis plate is already affixed to an adjacent bone segment. In this embodiment, the screws holding the previously implanted plate to the adjacent bone segment are removed and the thin portion of the extension plate is inserted underneath the previously implanted plate such that the screw holes of the previously implanted plate and the screw holes of the extension plate are in alignment. The screws are then reinserted into the bone through the previously implanted plate and the thin portion of the extension plate. The thick portion of the extension plate is screwed into the adjacent bone segment thereby immobilizing the adjacent bone segment. In this manner, a bone segment adjacent to a previously injured and immobilized bone segment can be immobilized without completely removing a previously implanted plate. In other words, only the screws holding the previously implanted plate to the adjacent bone segment are removed, not all screws holding the previously implanted plate to all the previously immobilized bone segments need be removed.

In a further embodiment of the invention, the thick portion of the extension plate may have more than one row of through openings for immobilization of more than one adjacent bone segment. In this embodiment, the extension plate has a greater longitudinal dimension in order to extend over more than one adjacent bone segment. Pairs of holes are positioned such that each adjacent bone segment can be affixed by two bone screws. The number of adjacent bone segments that can be immobilized in this manner may be two, three, four or more.

In a further embodiment of the invention, the through openings are elongated slots. The elongated slots provide for ease of positioning and alignment of the extension plate, particularly when the extension plate is used in connection with a non-identical previously implanted plate or when the respective bone segments to be immobilized are not of uniform dimension.

In another embodiment of the invention, the elongated slots arranged in the thin portion of the plate are open-ended at the transverse edge of the thin portion of the plate. Such a configuration enables the extension plate to be affixed between a bone segment and a previously implanted plate without complete removal of the bone screws of the previously implanted plates. In such a configuration, the screws holding the previously implanted plate to the bone segment adjacent to the injured bone segment need only be loosened such that the thin portion of the extension plate can be slid into position. The extension plate is inserted between the bone segment and the previously implanted plate such that the open-ended slots of the thin portion of the extension plate fit around the loosened screws of the previously implanted plate. The screws are then re-tightened and the thick portion of the extension plate is screwed into the adjacent bone segment. In this manner, a bone segment adjacent to a previously injured and immobilized bone segment can be immobilized without completely removing the screws from a previously implanted plate.

In a further embodiment of the invention, the open-ended slots have beveled edges for ease of insertion underneath a previously implanted plate.

In another embodiment of the invention, the thin plate portion of the extension plate is provided with side rails arranged at the longitudinal edges of the thin plate portion which extend above the second non-bone contacting surface of the extension plate. When the extension plate is positioned underneath the second osteosynthesis plate the side rails are substantially parallel to edge surfaces of the second osteosynthesis plate.

The side rails may interlock with grooves cut into the edge surfaces of the second osteosynthesis plate.

In an alternate embodiment of the invention, the extension plate is generally defined by contoured longitudinal and transverse edges. The thick plate portion has at least one row of pairs of through openings. The thin plate portion has at least one through opening. The thick plate portion of this embodiment has a substantially larger transverse dimension than the thin plate portion. The thin plate portion is dimensioned to fit within a groove provided in a non-bone contacting surface of a second osteosynthesis plate such that the thin plate portion can be affixed to a non-bone contacting surface of the second osteosynthesis plate without the need to remove existing screws affixing the second osteosynthesis plate. The thin plate portion of the extension plate may be affixed to the second plate by means of one or more screws and the thick plate portion may be affixed to the adjacent bone segments by means of one or more screws. The thin plate portion of the extension plate in this embodiment may comprise a T-shaped portion extending from the thin plate portion which fits within a corresponding groove in the second plate.

In a further embodiment, the extension plate has a plate portion having at least one row of pairs of through openings with two extension arms extending longitudinally from the plate portion. The extension arms are dimensioned to fit alongside a second osteosynthesis plate. The plate portion may be affixed to the second osteosynthesis plate by a clamping device and to the adjacent bone segment by screws.

In an alternate example embodiment, a groove may be provided in each of the extension arms for accommodating lengthwise edge surfaces of the second osteosynthesis plate when the extension plate is positioned adjacent the second osteosynthesis plate. The groove may extend from a tip of one extension arm to a tip of the other extension arm.

A contoured section may be provided which extends between a base of each extension arm. The contoured section may be adapted to conform to a contoured transverse edge of the second osteosynthesis plate.

An additional single through opening may be positioned in a center portion of the plate portion above the at least one row of pairs of through openings. Bone screws may be inserted through the at least one row of through openings and through the single through opening for securing the extension plate in place in a bone segment and adjacent the second osteosynthesis plate.

The through openings may comprise elongated slots.

Multiple extension plates may be used to immobilize multiple adjacent bone segments.

BRIEF DESCRIPTION OF THE DRAWINGS

FIG. 24 shows a further embodiment of the extension plate;

FIG. 25 shows a side view of the extension plate of FIG. 24;

FIG. 26 shows a perspective view of the extension plate of FIG. 24;

FIG. 36 shows a bottom perspective view of the extension plate of FIG. 33 attached to a second osteosynthesis plate.

DETAILED DESCRIPTION OF THE INVENTION

The invention relates to a method and apparatus for immobilizing adjacent bone segments. An osteosynthesis plating system is provided for fixing or immobilizing several pieces or segments of bone utilizing screws which may be screwed into the segments of bone through openings provided in the osteosynthesis plate. The osteosynthesis plate is pressed against the bone surface by the screws and fixed thereto. In particular, the invention relates to an osteosynthesis extension plate for immobilizing adjacent segments of bone in a second surgery wherein the removal of a previously implanted osteosynthesis plate is avoided. In this manner the disadvantages associated with removal of the previously implanted plate are avoided.

Therefore, the advantages provided by the present invention include a reduction in surgery time and a less invasive surgical procedure. In addition, the cost associated with the extension plate is lower compared to a longer replacement plate. Surgical costs are decreased as well due to the reduction in surgical time required.

Figure 1:
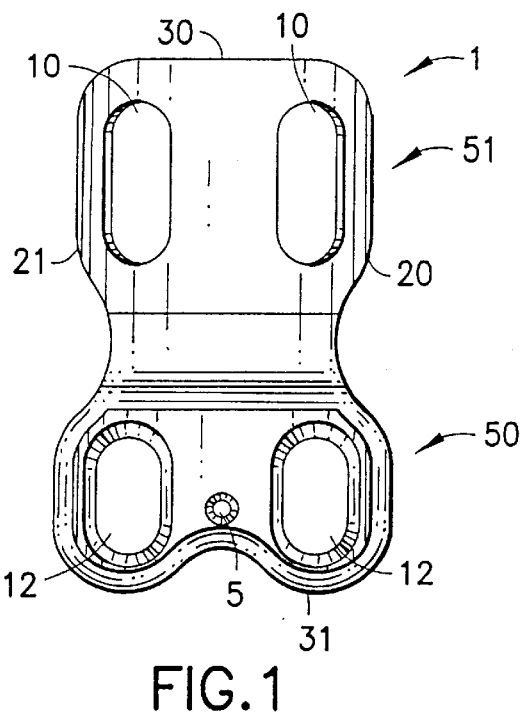
FIG. 1 shows an embodiment of the extension plate.
Figure 2:
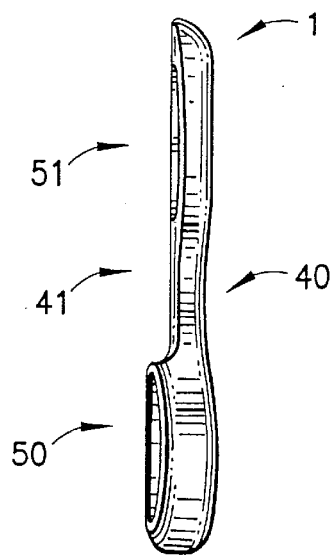
FIG. 2 shows a side view of the extension plate of FIG. 1.

FIG. 1 shows a particular embodiment of the osteosynthesis extension plate 1. The extension plate 1 is provided for immobilizing at least two adjacent bone segments by means of screws which may be screwed into the bone segments through openings 10, 12 in the extension plate. The extension plate is generally defined by longitudinal edges 20, 21 and transverse edges 30, 31, the plate having a greater longitudinal dimension than transverse dimension. FIG. 2 shows the extension plate of FIG. 1 from a side view. The extension plate 1 has a first bone contacting surface 40 and a second non-bone contacting surface 41. The extension plate is further defined by a thick plate portion 50 and a thin plate portion 51. At least two rows of pairs of through openings are provided in the extension plate.

As shown in FIG. 1, a first pair of through openings 12 is arranged in the thick portion 50 of the plate and a second pair of through openings 10 is arranged in the thin portion 51 of the plate such that the thin portion of the plate 51 can be inserted underneath and affixed between a second osteosynthesis plate and a bone segment. The thick portion 50 of the extension plate is affixed to an adjacent bone segment by screws, thereby immobilizing an adjacent bone segment.

In a further embodiment of the invention, the thin portion 51 of the extension plate can be positioned underneath the thick portion of an identical extension plate 1 to provide for immobilization of adjacent bone segments. In this manner several identical extension plates can be piggybacked by placing the thin portion 51 of one extension plate underneath the thick portion 50 of another extension plate to immobilize several adjacent bone segments.

A small through hole 5 may be provided to allow insertion of a positioning pin or tack through the extension plate 1 into the bone segment to temporarily secure the positioning of the extension plate while the screw holes are marked on the bone segment or drilled into the bone segment.

Figure 3:
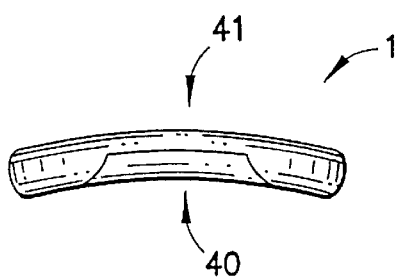
FIG. 3 shows an end view of the extension plate of FIG. 1.

In another embodiment of the invention as shown in FIG. 3, the extension plate 1 is curved in the direction transverse to its longitudinal axis such that the first bone contacting surface 40 is concave. Such a configuration of the first bone contacting surface 40 allows for better contact with the surface of the bone segment to be immobilized.

In a further embodiment of the invention, the osteosynthesis extension plate 1 is used to immobilize bone segments during a second surgery where a previously implanted osteosynthesis plate is already affixed to an adjacent bone segment. In this embodiment, the screws holding the previously implanted plate to the adjacent bone segment are removed and the thin portion 51 of the extension plate 1 is inserted underneath the previously implanted plate such that the screw holes of the previously implanted plate and the screw holes 10 of the thin portion 51 of the extension plate are in alignment. Screws are then reinserted into the bone segment through the previously implanted plate and the thin portion 51 of the extension plate. The thick portion 50 of the extension plate is screwed into the adjacent bone segment thereby immobilizing the adjacent bone segment. In this manner, a bone segment adjacent to a previously injured and immobilized bone segment can be immobilized without completely removing a previously implanted plate. In other words, only the screws holding the previously implanted plate to the adjacent bone segment are removed, not all screws holding the previously implanted plate to all the previously immobilized bone segments need be removed. A perspective view of the extension plate of FIG. 1 is shown in FIG. 4.

Figure 4:
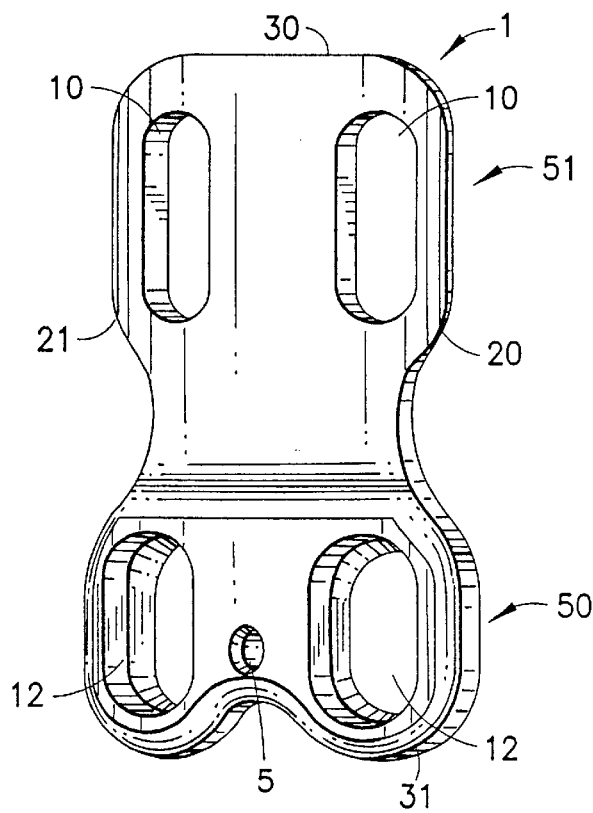
FIG. 4 shows a perspective view of the extension plate of FIG. 1.

In a further embodiment of the invention, the through openings 10, 12 are elongated slots as shown in FIGS. 1 and 4. The elongated slots provide for ease of positioning and alignment of the extension plate, particularly when the extension plate is used in connection with a non-identical previously implanted plate or when the respective bone segments to be immobilized are not of uniform dimension.

Figure 5:
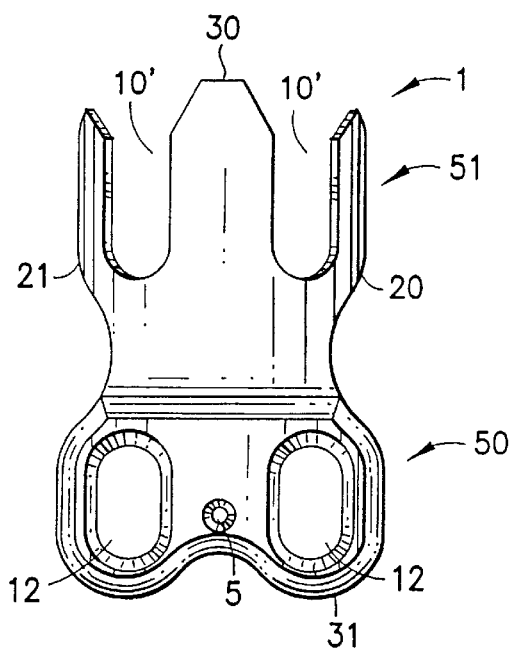
FIG. 5 shows a further embodiment of the extension plate.

In another embodiment of the invention as shown in FIG. 5, the elongated slots arranged in the thin portion 51 of the plate are open-ended slots 10' at the transverse edge 30 of the thin portion 51 of the plate. Such a configuration enables the extension plate 1 to be affixed between a bone segment and a previously implanted plate without complete removal of the bone screws of the previously implanted plates. In such a configuration, the screws holding the previously implanted plate to the bone segment adjacent to the injured bone segment need only be loosened such that the thin portion 51 of the extension plate can be slid into position. The extension plate 1 is inserted between the bone segment and the previously implanted plate such that the open-ended slots 10' of the thin portion 51 of the extension plate fit around the loosened screws of the previously implanted plate. The screws are then re-tightened and the thick portion of the extension plate 50 is screwed into the adjacent bone segment. In this manner, a bone segment adjacent to a previously injured and immobilized bone segment can be immobilized without completely removing the screws from a previously implanted plate.

Figure 6:
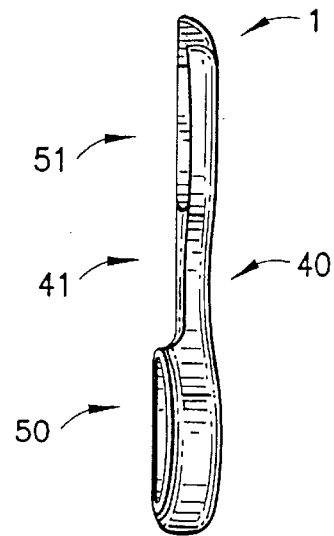
FIG. 6 shows a side view of the extension plate of FIG. 5.
Figure 7:
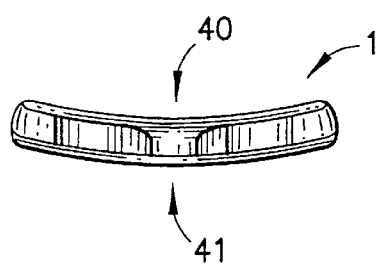
FIG. 7 shows an end view of the extension plate of FIG. 5.
Figure 8:
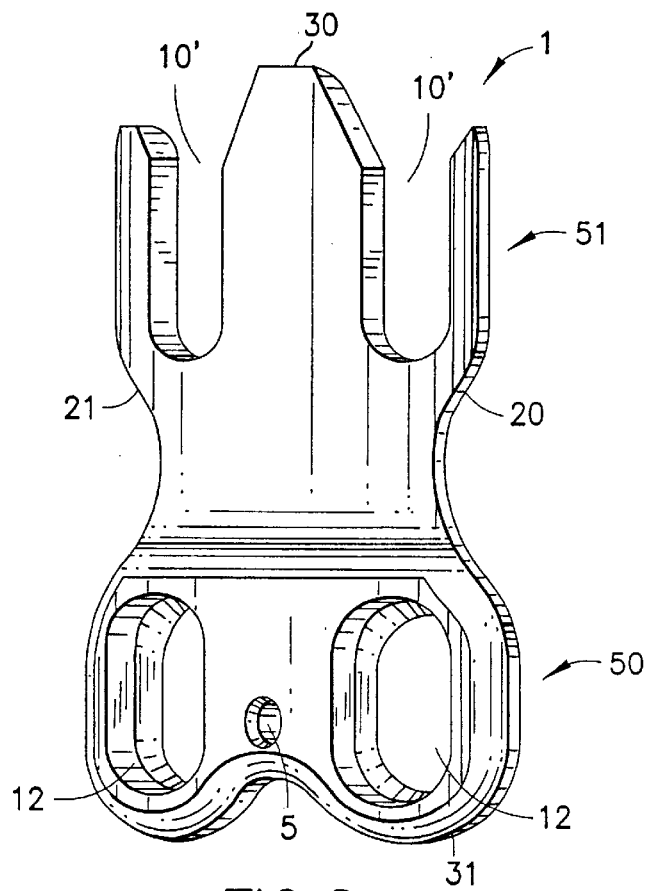
FIG. 8 shows a perspective view of the extension plate of FIG. 5.

A side view of the extension plate of FIG. 5 is shown in FIG. 6. An end view is shown in FIG. 7 and a perspective view is shown in FIG. 8.

In a further embodiment of the invention, the open-ended slots 10' have beveled edges for ease of insertion underneath a previously implanted plate.

Figure 9:
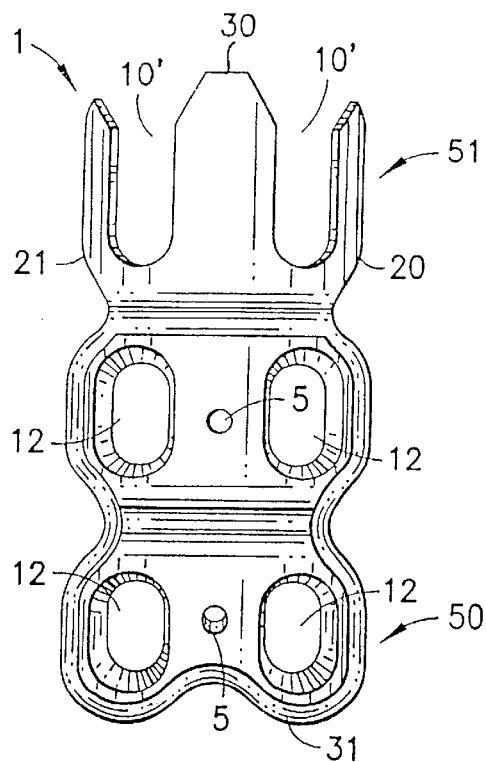
FIG. 9 shows a further embodiment of the extension plate.
Figure 10:
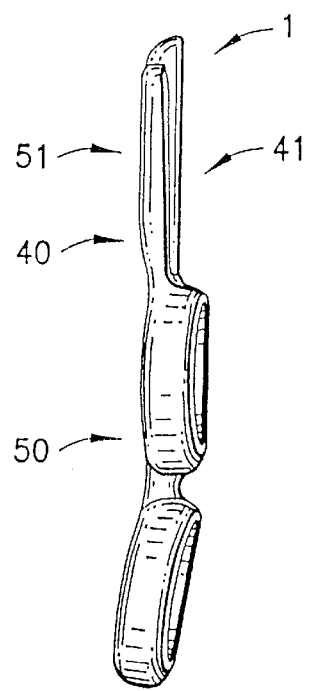
FIG. 10 shows a side view of the extension plate of FIG. 9.
Figure 11:
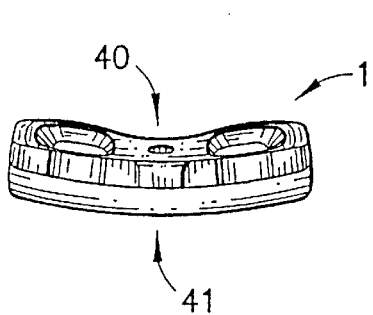
FIG. 11 shows an end view of the extension plate of FIG. 9.
Figure 12:
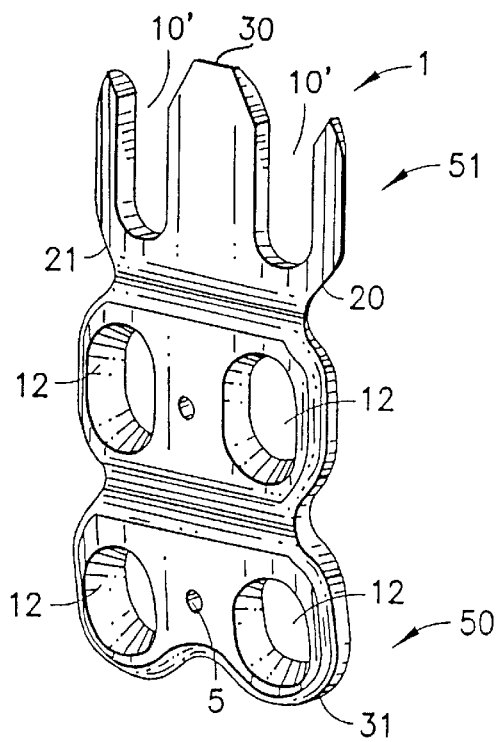
FIG. 12 shows a perspective view of the extension plate of FIG. 9.

In a further embodiment of the invention as shown in FIG. 9, the thick portion 50 of the extension plate may have more than one row of through openings 12 for immobilization of more than one adjacent bone segment. In this embodiment, the extension plate 1 has a greater longitudinal dimension in order to extend over more than one adjacent bone segment. Pairs of holes are positioned such that each adjacent bone segment can be affixed by two bone screws. The number of adjacent bone segments that can be immobilized in this manner may be two, three, four or more. A side view of the extension plate of FIG. 9 is shown in FIG. 10. An end view is shown in FIG. 11 and a perspective view is shown in FIG. 12.

Figure 13:
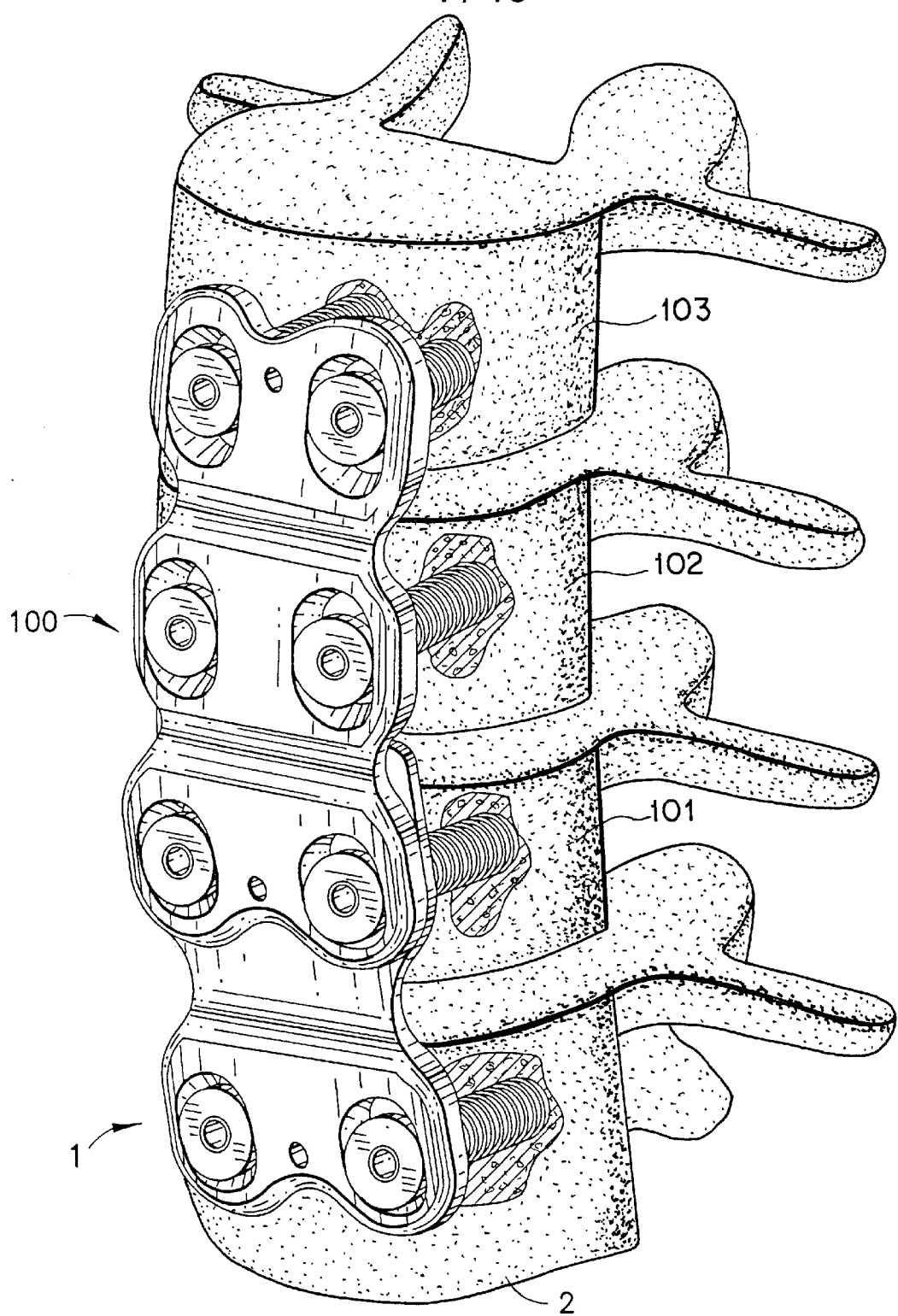
FIG. 13 shows a perspective view of the extension plate attached to a bone segment.

FIG. 13 shows a perspective view of the extension plate 1 attached to a bone segment 2 and inserted between a previously implanted bone plate 100 and an adjacent bone segment 101. The extension plate 1 in FIG. 13 may include any of the embodiments described herein. The previously implanted bone plate is shown attached to three bone segments 101, 102, and 103.

Figure 14:
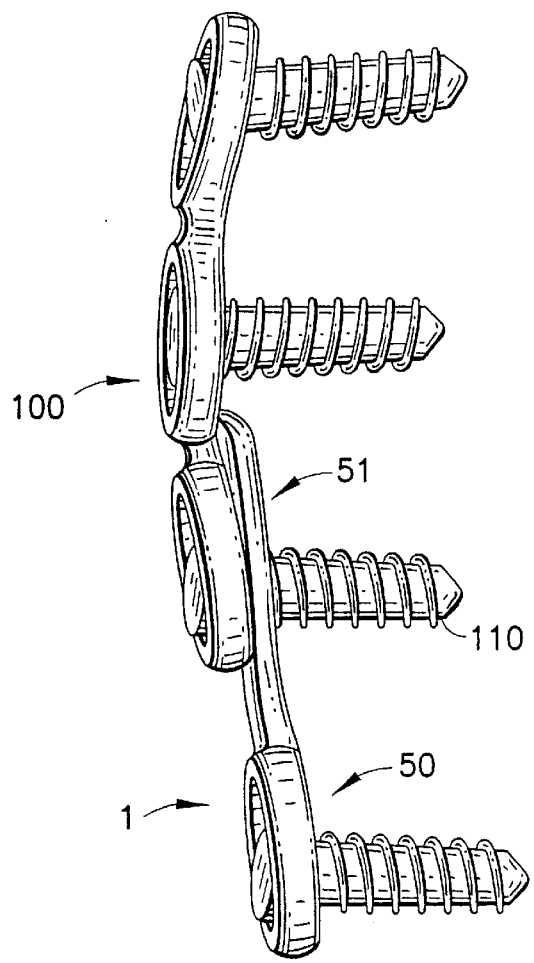
FIG. 14 shows a side view of the extension plate attached to a second osteosynthesis plate.

FIG. 14 shows a side view of an extension plate 1 connected to a previously implanted bone plate 100. The thin portion 51 of the extension plate is shown inserted underneath the previously implanted bone plate 100 such that the bone screws 110 can be inserted through the screw holes of the previously implanted plate 100 and the screw holes or open-ended slots of the extension plate 1.

Figure 15:
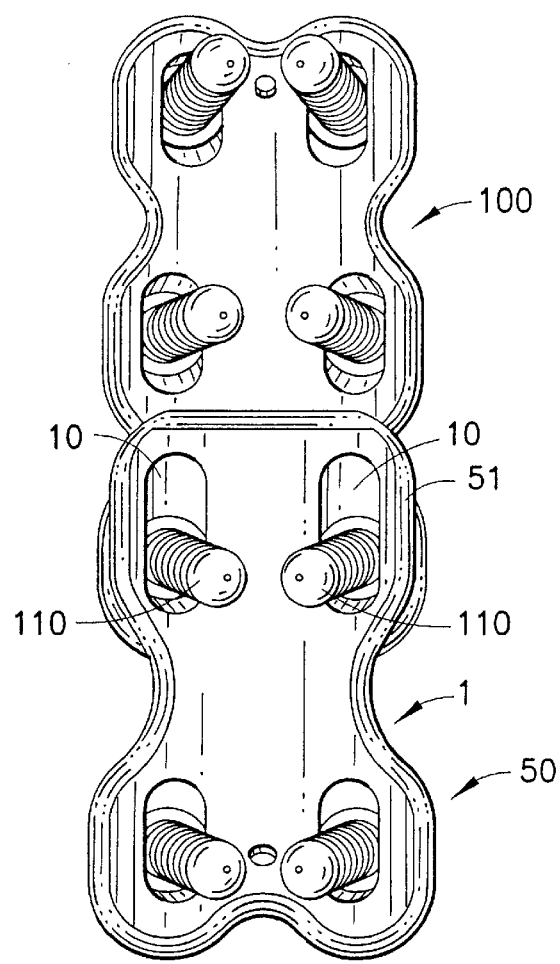
FIG. 15 shows a bottom perspective view of the extension plate attached to a second osteosynthesis plate.
Figure 16:
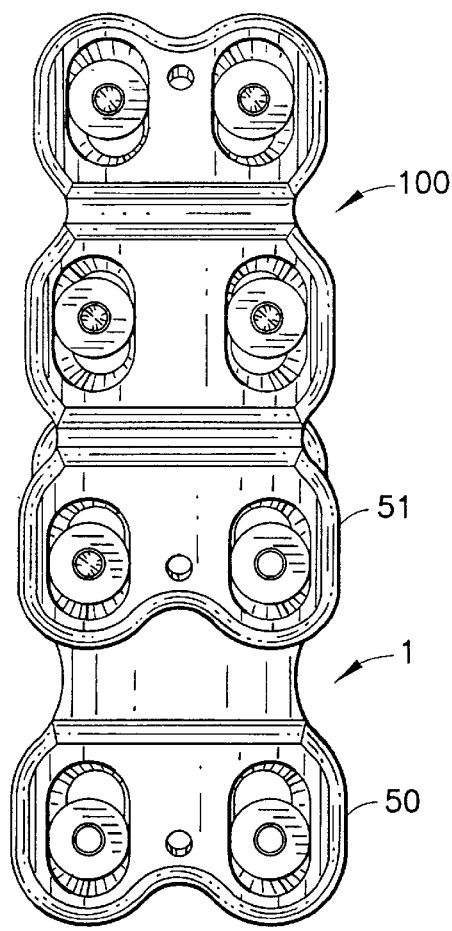
FIG. 16 shows a top view of the extension plate attached to a second osteosynthesis plate.
Figure 17:
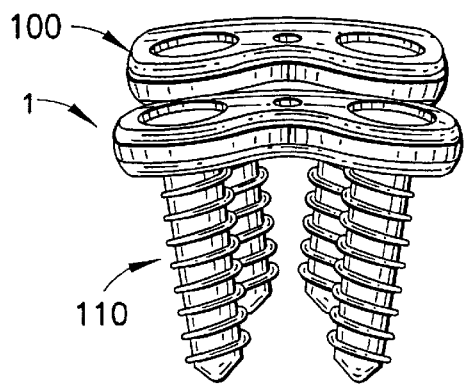
FIG. 17 shows an end perspective view of the extension plate attached to a second osteosynthesis plate.
Figure 18:
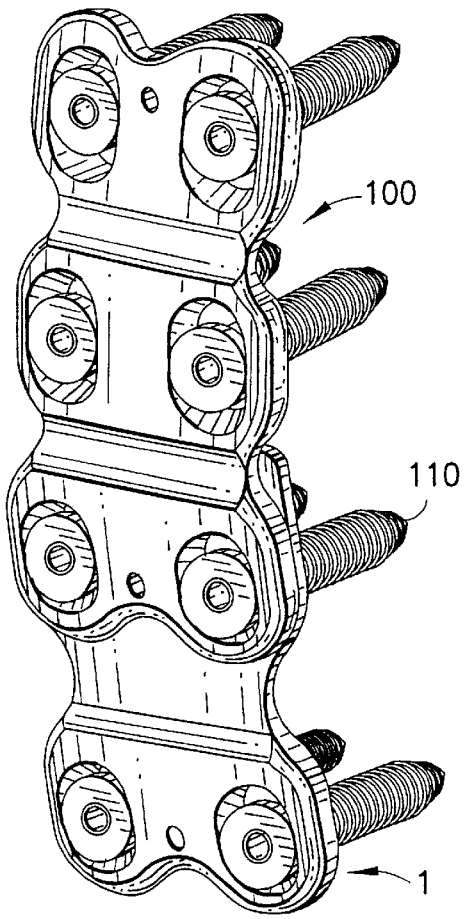
FIG. 18 shows a perspective view of the extension plate attached to a second osteosynthesis plate.

FIG. 15 provides a bottom view of the configuration of FIG. 14. In the embodiment shown, the extension plate 1 has elongated slots 10. However, any of the embodiments discussed above may be used in this configuration, including the open-ended slot configuration of FIG. 5. FIG. 15 more clearly shows the alignment of the screws 110. FIG. 16 shows a top view of the FIG. 15 embodiment. In FIG. 16 the positioning of the thin portion 51 of the extension plate 1 underneath the previously implanted plate 100 can be seen. FIG. 17 shows an end view of this configuration and FIG. 18 shows a perspective view.

Figure 19:
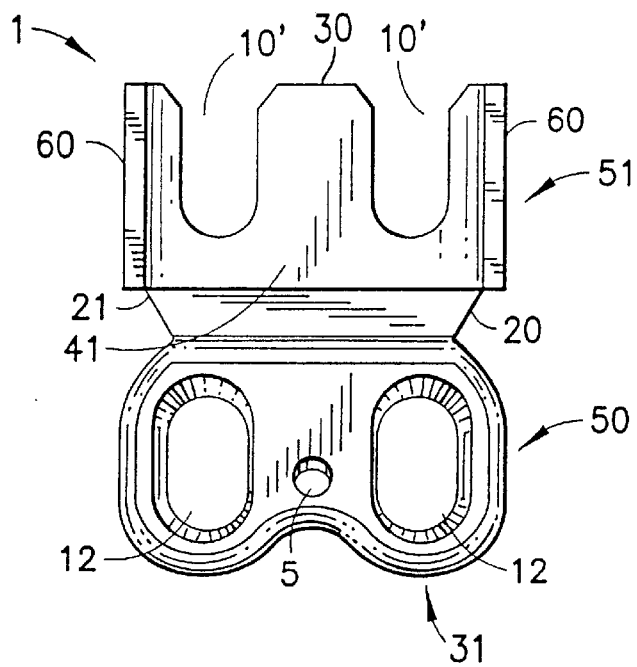
FIG. 19 shows a further embodiment of the extension plate.
Figure 20:
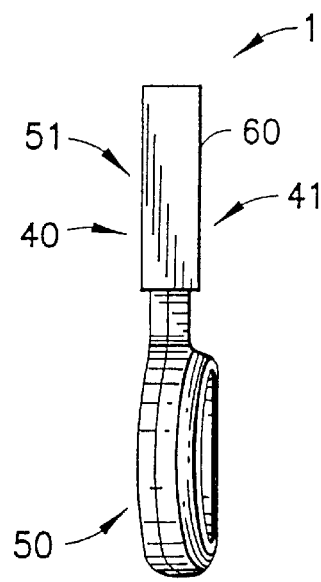
FIG. 20 shows a side view of the extension plate of FIG. 19.
Figure 21:
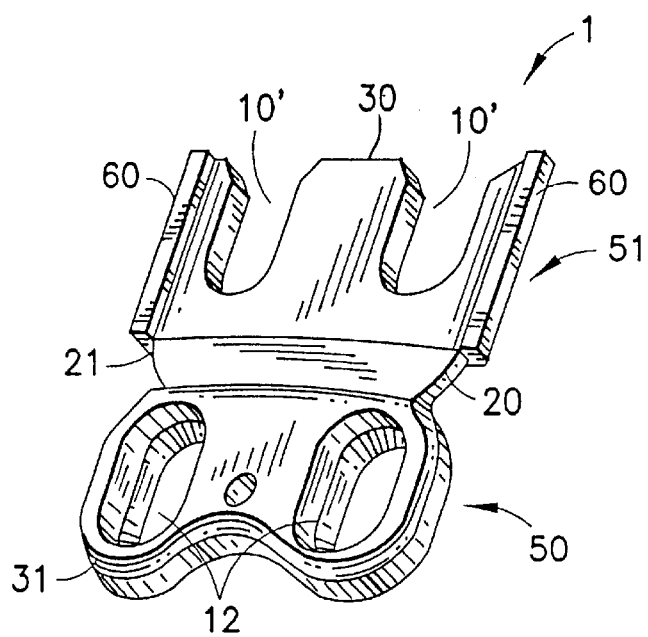
FIG. 21 shows a perspective view of the extension plate of FIG. 19.
Figure 22:
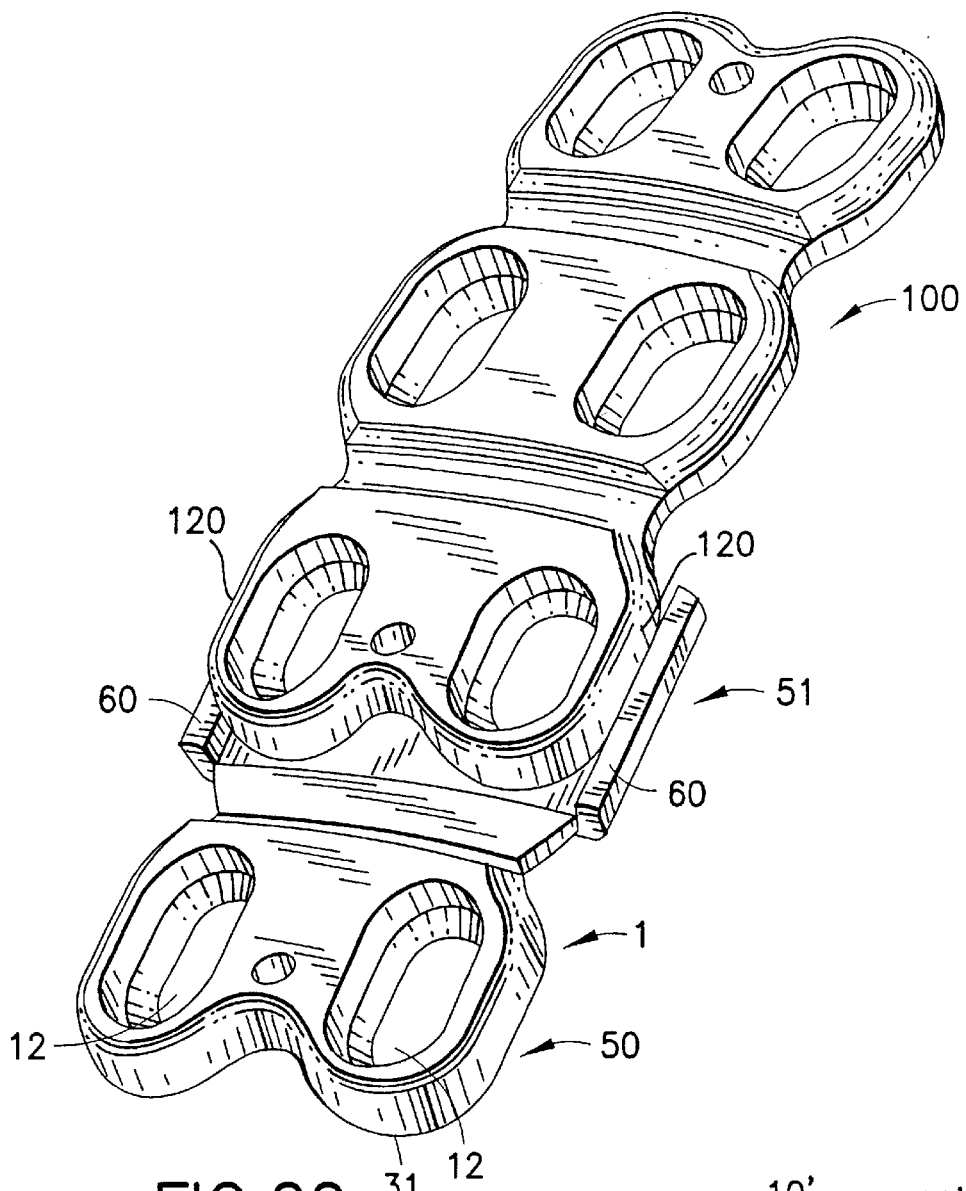
FIG. 22 shows a perspective view of the extension plate of FIG. 19 attached to a second osteosynthesis plate.

In another embodiment of the invention as shown in FIG. 19, the thin plate portion 51 of the extension plate 1 is provided with side rails 60 arranged at the longitudinal edges 20, 21 of the thin plate portion 51 which side rails extend above the second non-bone contacting surface 41 of the extension plate 1. A side view of the extension plate of FIG. 19 is shown in FIG. 20 and a perspective view is shown in FIG. 21. As shown in FIG. 22, when the extension plate 1 is positioned underneath the second osteosynthesis plate 100 the side rails 60 are substantially parallel to edge surfaces 120 of the second osteosynthesis plate 100. The side rails 60 act to increase the bending strength of the extension plate 1 and enable a close fit with the second osteosynthesis plate 100.

Figure 23:
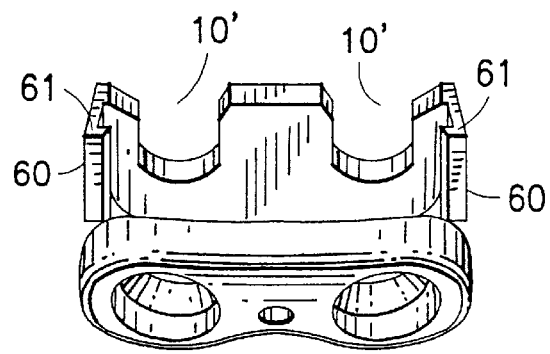
FIG. 23 shows a further embodiment of the extension plate of FIG. 19.

FIG. 23 shows an alternate embodiment of the extension plate shown in FIG. 19. The side rails 60 may have ridges 61 which can interlock with grooves cut into the edge surfaces 120 of the second osteosynthesis plate 100.

Figure 27:
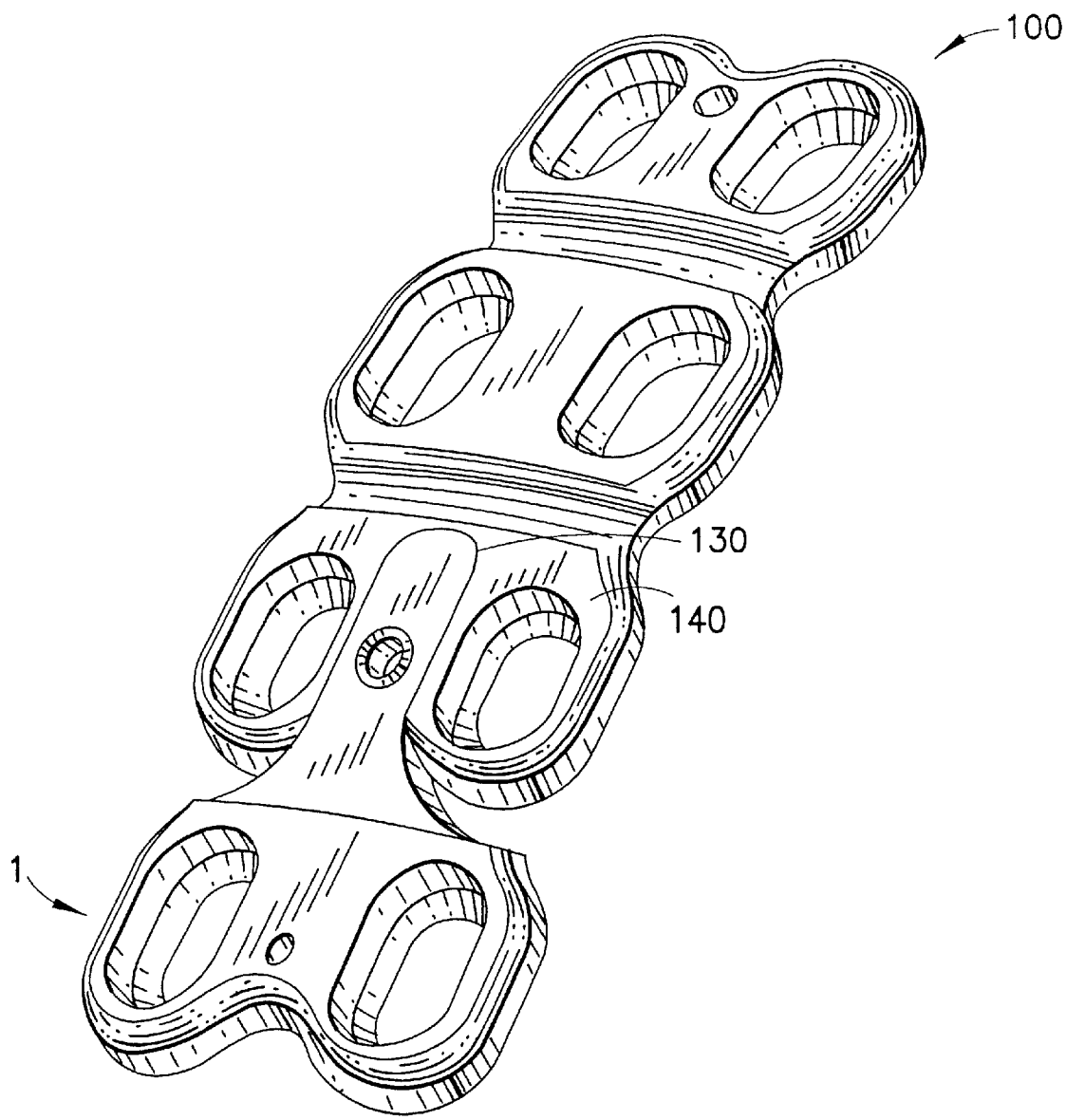
FIG. 27 shows a perspective view of the extension plate of FIG. 24 attached to a second osteosynthesis plate.

In an alternate embodiment of the invention as shown in FIG. 24, the extension plate 1 is generally defined by contoured longitudinal edges 20', 21' and contoured transverse edges 30', 31'. The thick plate portion 50 has at least one row of pairs of through openings 12. The thin plate portion 51' has at least one through opening 11. The thick plate portion 50 has a substantially larger transverse dimension than the thin plate portion 51'. A side view of the plate 1 of FIG. 24 is shown in FIG. 25 and a perspective view is shown in FIG. 26. As shown in FIG. 27, the thin plate portion 51' is dimensioned to fit within a groove 130 provided in a non-bone contacting surface 140 of a second osteosynthesis plate 100. Such an arrangement reduces the overall thickness of the implant as the thin plate portion 51' fits substantially within the groove 130 provided in the second plate 100. In addition, with the extension plate of FIG. 24, there is no need to remove or loosen the screws holding the previously implanted second plate 100 as the extension plate fits in a groove 130 on the non-bone contacting surface 140 of the second plate 100. The extension plate may be affixed to the second plate 100 by means of a screw through the opening 11 and to the adjacent bone segment by means of screws through the openings 12.

Figure 28:
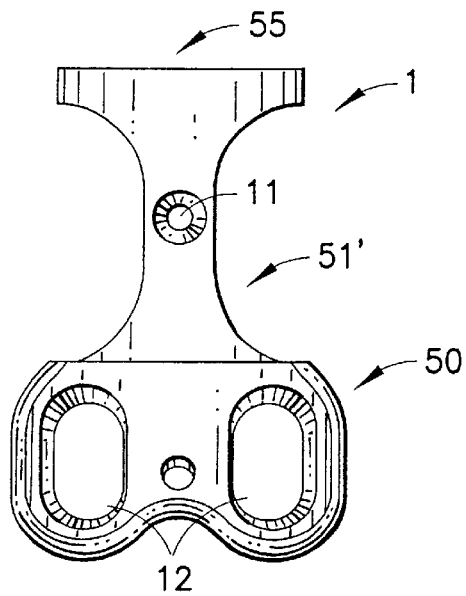
FIG. 28 shows a further embodiment of the extension plate of FIG. 24.
Figure 29:
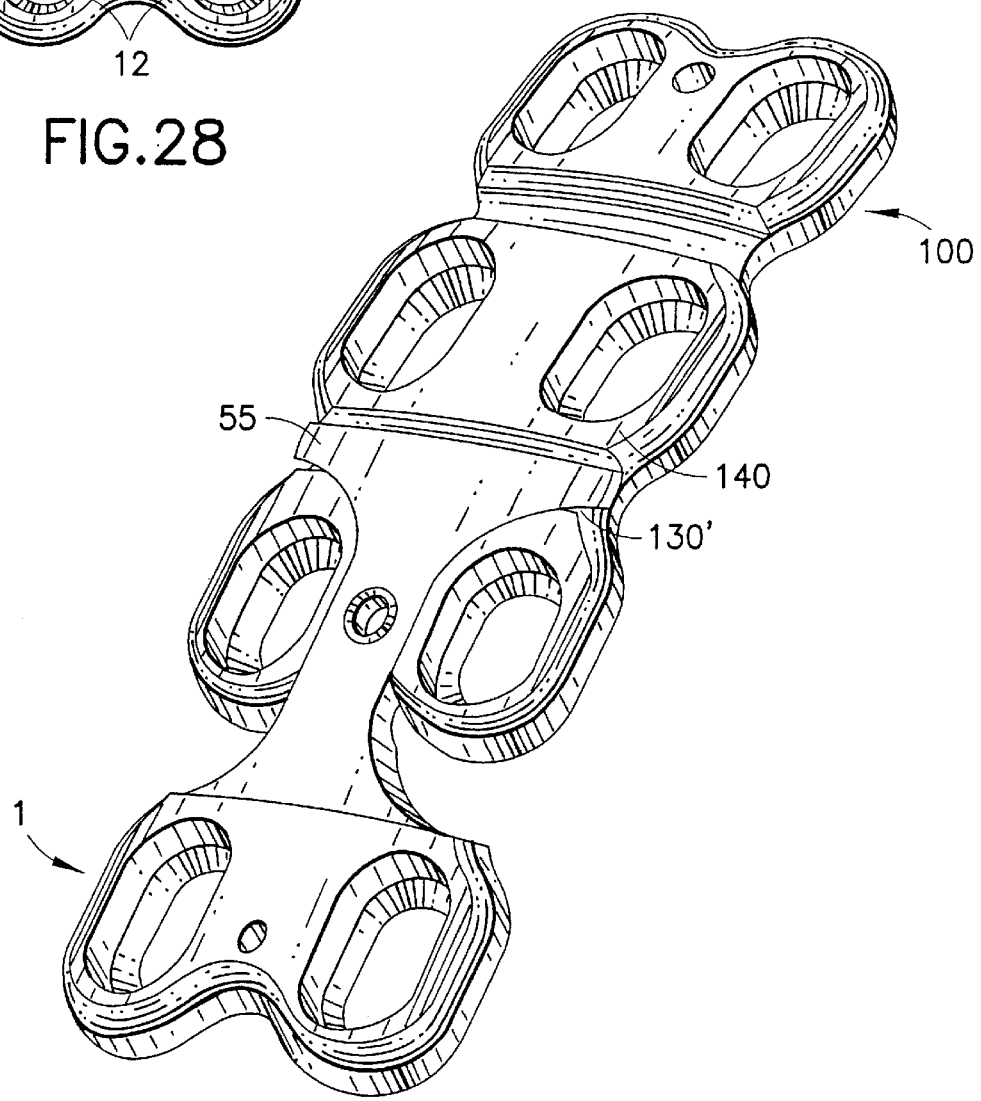
FIG. 29 shows a perspective view of the extension plate of FIG. 28 attached to a second osteosynthesis plate.

Alternatively, the thin plate portion 51' of the extension plate 1 of FIG. 24 may comprise a T-shaped portion 55 extending from the thin plate portion 51' as shown in FIG. 28. As shown in FIG. 29, the T-shaped portion 55 fits within a corresponding groove 130' in a non-bone contacting surface 140 of the second plate 100.

Figure 30:
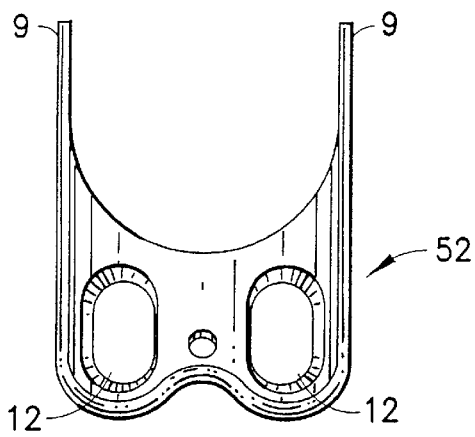
FIG. 30 shows a further embodiment of the extension plate.
Figure 31:
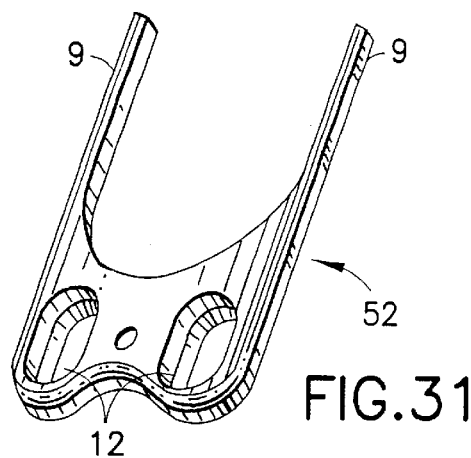
FIG. 31 shows a perspective view of the extension plate of FIG. 30.
Figure 32:
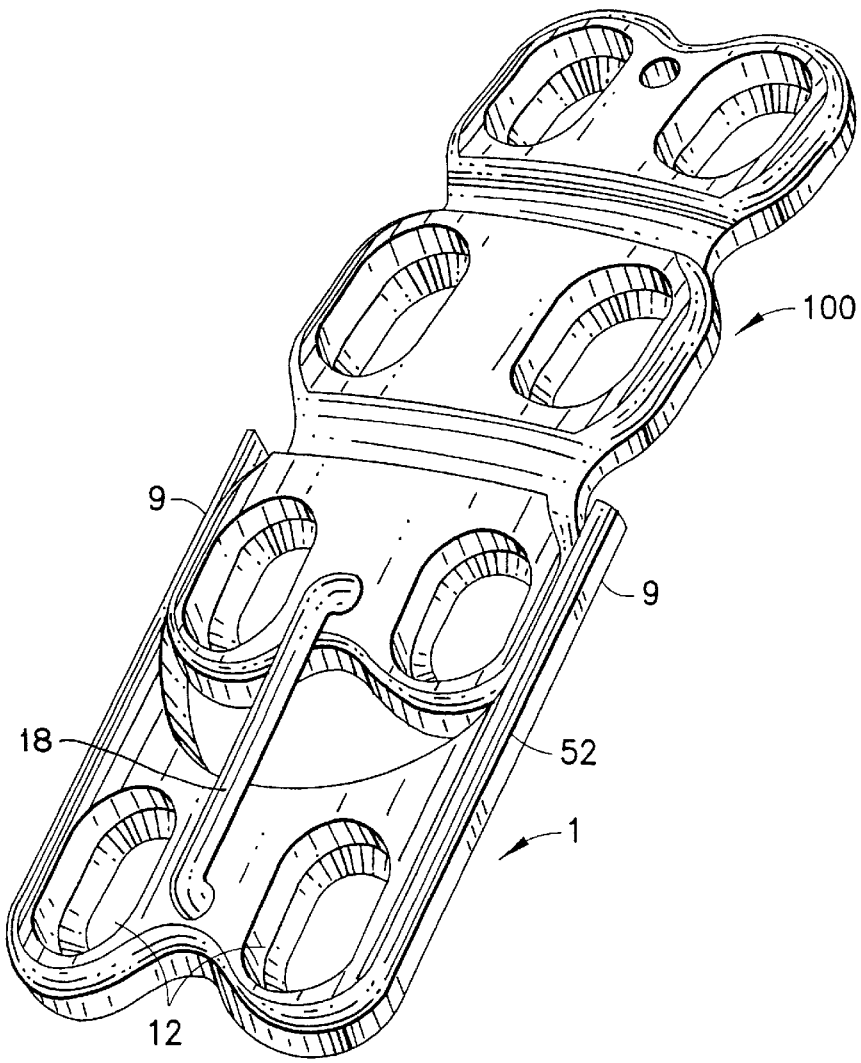
FIG. 32 shows a perspective view of the extension plate of FIG. 30 attached to a second osteosynthesis plate.

In a further embodiment shown in FIG. 30, the extension plate has a plate portion 52 having at least one row of pairs of through openings 12 with two extension arms 9 extending longitudinally from the plate portion 52. A perspective view of the extension plate of FIG. 30 is shown in FIG. 31. As shown in FIG. 32, the extension arms 9 are dimensioned to fit alongside a second osteosynthesis plate 100. The plate portion 52 can be affixed to the second osteosynthesis plate 100 by a device 18 such as a clamp or similar device and to an adjacent bone segment by screws. Such an arrangement provides the required stiffness and stability under flexion and extension of the bone segments. With such an arrangement, there is no need to loosen or remove any screws from the previously implanted bone plate 100. With the extension plate of FIG. 30, it may be necessary to cut a small channel or groove in the bone segment alongside the previously implanted bone plate 100 to provide room for the extension arms 9. Such a groove or channel can be cut in the bone segment using a high speed burr or similar instrument.

Figure 33:
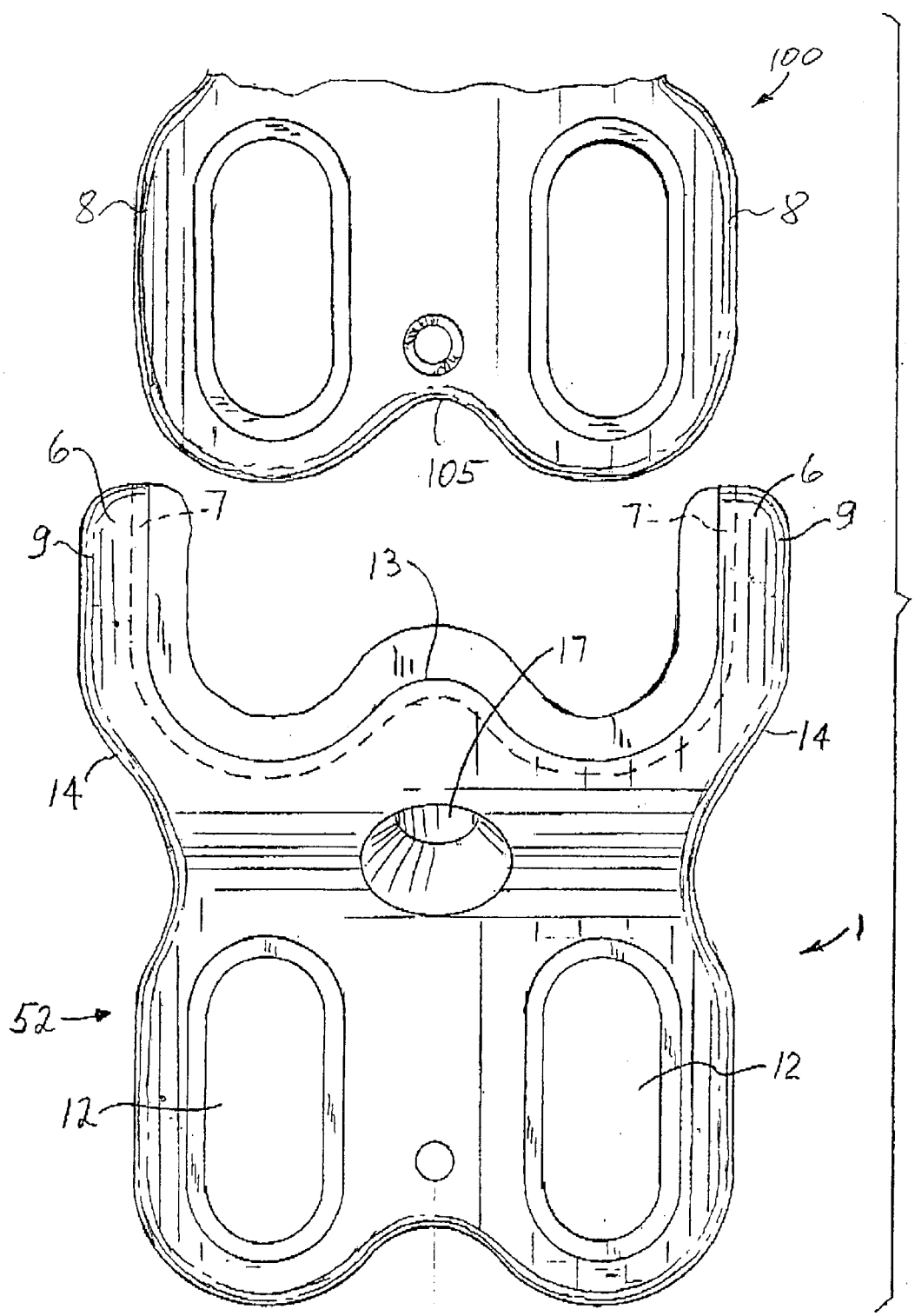
FIG. 33 shows a further example embodiment of the extension plate.
Figure 34:
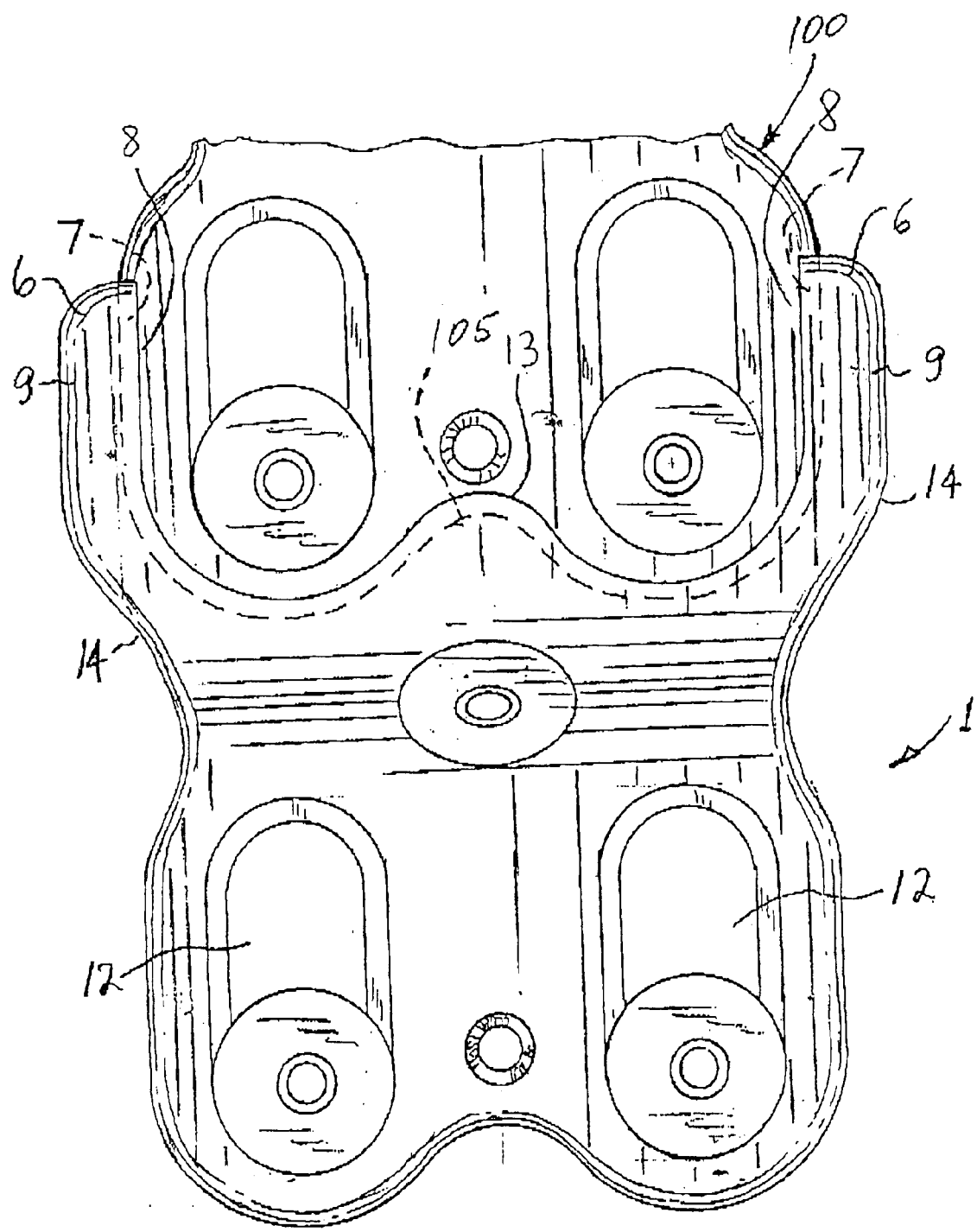
FIG. 34 shows the extension plate of FIG. 33 attached to a second osteosynthesis plate.

An alternate example embodiment of the invention is shown in FIGS. 33 and 34. FIG. 33 shows the extension plate 1 separated from the second osteosynthesis plate 100, while FIG. 34 shows the extension plate 1 connected to the second osteosynthesis plate 100. In this example embodiment, a groove 7 may be provided in each of the extension arms 9. The grooves 7 are adapted to accommodate lengthwise edge surfaces 8 of the second osteosynthesis plate 100 when the extension plate 1 is positioned adjacent the second osteosynthesis plate 100, which may be, for example, a previously implanted bone plate. The grooves 7 strengthen the connection between the previously implanted bone plate 100 and the extension plate 1. In such an embodiment, a previously implanted bone plate may be used which is not specifically adapted to the extension plate, as long as the grooves 7 in the extension arms 9 accommodate the edges of the previously implanted bone plate 100.

The groove 7 may extend from a tip 6 of one extension arm 9 to a tip 6 of the other extension arm 9. In other words, the groove 7 extends over the entire point of contact between the second osteosynthesis plate 100 and the extension plate 1.

A contoured section 13 may be provided which extends between a base 14 of each extension arm 9. The contoured section 13 may be adapted to conform to a contoured transverse edge 105 of the second osteosynthesis plate 100. In such a configuration, the second osteosynthesis plate 100 and the extension plate 1 are in contact with each other not only over the length of the extension arms 9, but also over the area in between the extension arms 9.

An additional single through opening 17 may be positioned in a center portion of the plate portion above the at least one row of pairs of through openings 12. Bone screws 110 may be inserted through the at least one row of through openings 12 and through the single through opening 17 for securing the extension plate 1 in place in a bone segment and adjacent the second osteosynthesis plate 100.

Figure 35:
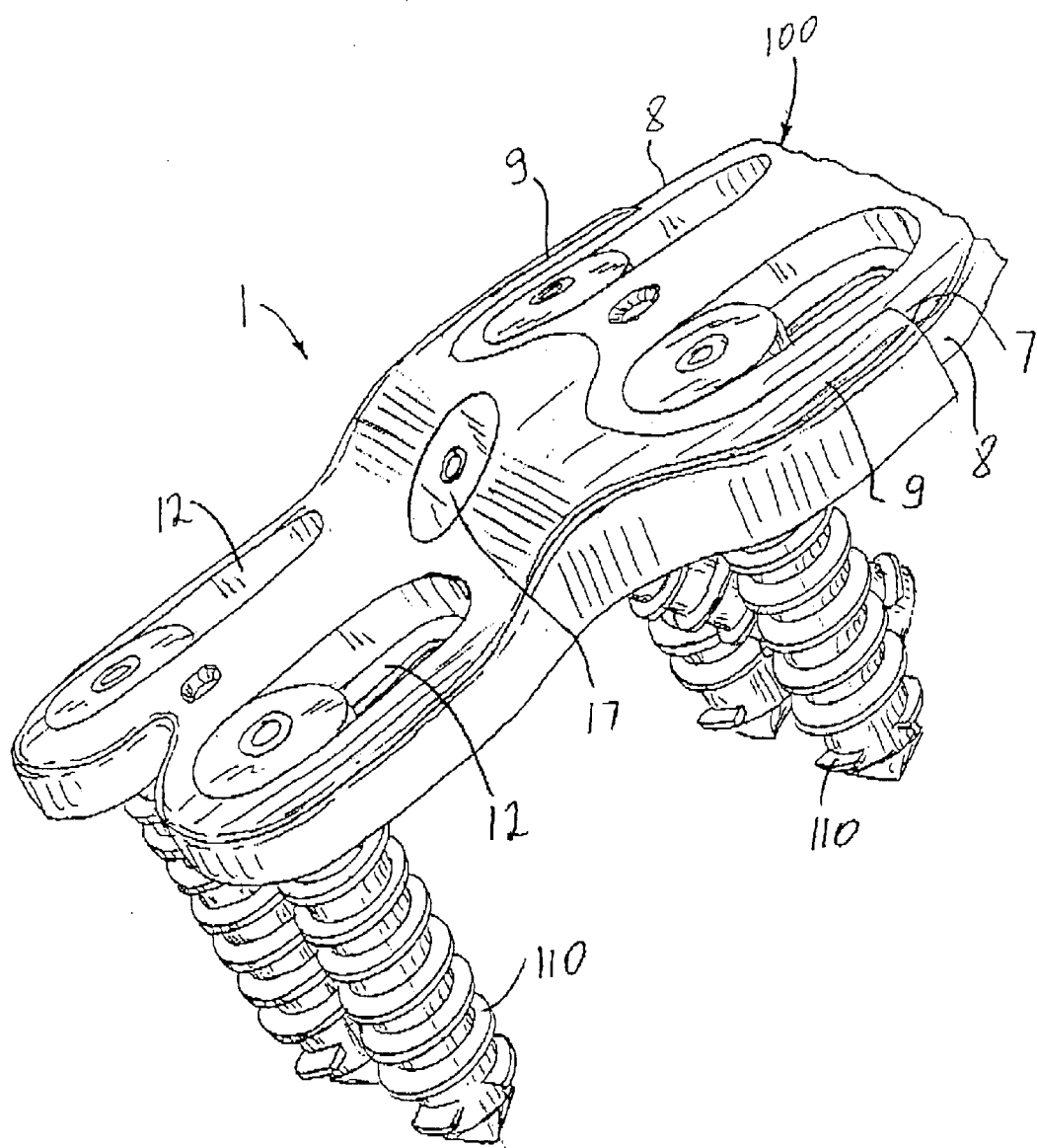
FIG. 35 shows a side perspective view of the extension plate of FIG. 33 attached to a second osteosynthesis plate.

FIG. 35 shows a side perspective view of the extension plate 1 attached to the second osteosynthesis plate 100. FIG.

36 shows a bottom perspective view of the extension plate 1 attached to the second osteosynthesis plate 100.

The through openings 12 may comprise elongated slots.

Multiple extension plates may be used to immobilize multiple adjacent bone segments.

It will now be appreciated that the present invention provides an improved method and apparatus for fixing or immobilizing several pieces or segments of bone utilizing screws which may be screwed into the segments of bone through openings provided in the osteosynthesis plate. In particular, the invention provides an improved method and apparatus for immobilizing adjacent segments of bone in a second surgery wherein the removal of a previously implanted osteosynthesis plate is avoided. In this manner the disadvantages associated with removal of the previously implanted plate are avoided.

Although the invention has been described in connection with preferred embodiments thereof, those skilled in the art will appreciate that numerous adaptations and modifications may be made thereto without departing from the spirit and scope of the invention, as set forth in the following claims.

What is claimed is:

1. An osteosynthesis extension plate for immobilizing at least two adjacent bone segments by means of screws which may be screwed into the bone segments through openings in the extension plate, wherein the extension plate comprises:
   contoured longitudinal edges;
   contoured transverse edges;
   a first bone contacting surface;
   a second non-bone contacting surface;
   a plate portion having at least one row of pairs of through openings; and
   two extension arms extending longitudinally from the plate portion, said arms being dimensioned to fit alongside a second osteosynthesis plate.

2. An extension plate in accordance with claim 1, wherein said extension plate is adapted to be affixed to the second osteosynthesis plate by a clamping device.

3. An extension plate in accordance with claim 1, further comprising:
   an additional single through opening positioned in a center portion of said plate portion above said at least one row of pairs of through openings.

4. An extension plate in accordance with claim 1, wherein said through openings comprise elongated slots.

5. An extension plate in accordance with claim 1, further comprising:
   a groove in each of said extension arms for accommodating lengthwise edge surfaces of the second osteosynthesis plate when said extension plate is positioned adjacent the second osteosynthesis plate.

6. An extension plate in accordance with claim 5, wherein said groove extends from a tip of one extension arm to a tip of the other extension arm.

7. An extension plate in accordance with claim 6, further comprising:
   a contoured section extending between a base of each extension arm, said contoured section adapted to conform to a contoured transverse edge of said second osteosynthesis plate.

8. A method for immobilizing at least two adjacent bone segments comprising the steps of:
   fixing a first portion of an osteosynthesis extension plate to a bone segment by screws which may be screwed into the bone segment through openings in the extension plate;
   fixing a second portion of the extension plate to an adjacent bone segment;
   wherein the extension plate comprises:
      contoured longitudinal edges;
      contoured transverse edges;
      a first bone contacting surface;
      a second non-bone contacting surface;
      a plate portion having at least one row of pairs of through openings; and
      two extension arms extending longitudinally from the plate portion, said arms being dimensioned to fit alongside a second osteosynthesis plate.

9. An extension plate in accordance with claim 8, wherein:
   said extension plate is adapted to be affixed to the second osteosynthesis plate by a clamping device.

10. An extension plate in accordance with claim 8, further comprising:
    an additional single through opening positioned in a center portion of said plate portion above said at least one row of pairs of through openings.

11. An extension plate in accordance with claim 8, wherein said through opening comprise elongated slots.

12. A method in accordance with claim 8, further comprising:
    a groove in each of said extension arms for accommodating lengthwise edge surfaces of the second osteosynthesis plate when said extension plate is positioned adjacent the second osteosynthesis plate.

13. A method in accordance with claim 12, wherein said groove extends from a tip of one extension arm to a tip of the other extension arm.

14. An extension plate in accordance with claim 13, further comprising:
    a contoured section extending between a base of each extension arm, said contoured section adapted to conform to a contoured transverse edge of said second osteosynthesis plate.

* * * * *